United States Patent [19]
Lechtken et al.

[11] Patent Number: 5,481,041
[45] Date of Patent: Jan. 2, 1996

[54] ISOLATION OF TRIPHENYLPHOSPHINE

[75] Inventors: Peter Lechtken, Frankenthal; Friedrich Sauer, Obersuelzen; Matthias Fankhaenel, Ludwigshafen; Dieter Hermeling, Frankenthal, all of Germany

[73] Assignee: BASF Aktiengesellschaft, Ludwigshafen, Germany

[21] Appl. No.: 285,098

[22] Filed: Aug. 3, 1994

[30] Foreign Application Priority Data

Aug. 11, 1993 [DE] Germany .................. 43 26 953.2

[51] Int. Cl.⁶ ............................................. C07F 9/50
[52] U.S. Cl. ................................................. 568/17
[58] Field of Search ................................... 568/17

[56] References Cited

U.S. PATENT DOCUMENTS

| | | | |
|---|---|---|---|
| 4,249,023 | 2/1981 | Broger | 568/17 |
| 4,285,304 | 8/1981 | Bryant et al. | 568/17 |
| 4,301,301 | 11/1981 | Fukui et al. | 568/17 |
| 4,710,583 | 12/1987 | Bryant et al. | 568/17 |
| 4,845,306 | 7/1989 | Puckette | 568/17 |

FOREIGN PATENT DOCUMENTS 1029924  5/1966  United Kingdom .................. 568/17

OTHER PUBLICATIONS

Chemical Engineering Series, Liquid Extraction, 1951, pp. 273–301, R. E. Freybal.
Chem. Ing. tech. 48, 1976, No. 3, pp. 177–189, M. Bohnet.
Ein Beitrag Zur Tropfenabscheidung . . . , F. Rebelein, pp. 1–3 (1988).
Chem.–Ing.–Tech. 61 (1989) Nr. 8, S. 597–610, E. Blass et al.

Primary Examiner—James H. Reamer
Attorney, Agent, or Firm—Keil & Weinkauf

[57] ABSTRACT

A process for isolating triphenylphosphine (TPP) from a triphenylphosphine/aluminum chloride complex dissolved in chlorobenzene by decomplexation, hydrolysis and extraction using water and subsequent separation of the liquid/liquid dispersion, which is composed of a TPP-containing chlorobenzene phase and of an containing Al and Cl compounds aqueous phase, into a TPP-containing chlorobenzene phase and into a TPP-free, aqueous phase, containing Al and Cl compounds, wherein water is dispersed in the chlorobenzene phase in a ratio of 0.6–0.95 kg of water per kg of chlorobenzene solution in a 1st mixing apparatus in such a way that the temperature resulting from the hydrolysis is in the range from 60° to 90° C., the dispersion being carried out with residence times of 5–30 minutes and energy densities of 2–10 kW/m³, a second dispersion is carried out in a 2nd mixing apparatus with residence times of 5–60 minutes and energy densities of 0.05–0.5 kW/m³, and the heavier TPP-containing chlorobenzene phase is separated from the lighter TPP-free, aqueous phase containing Al and Cl compounds in a phase separator.

2 Claims, 1 Drawing Sheet

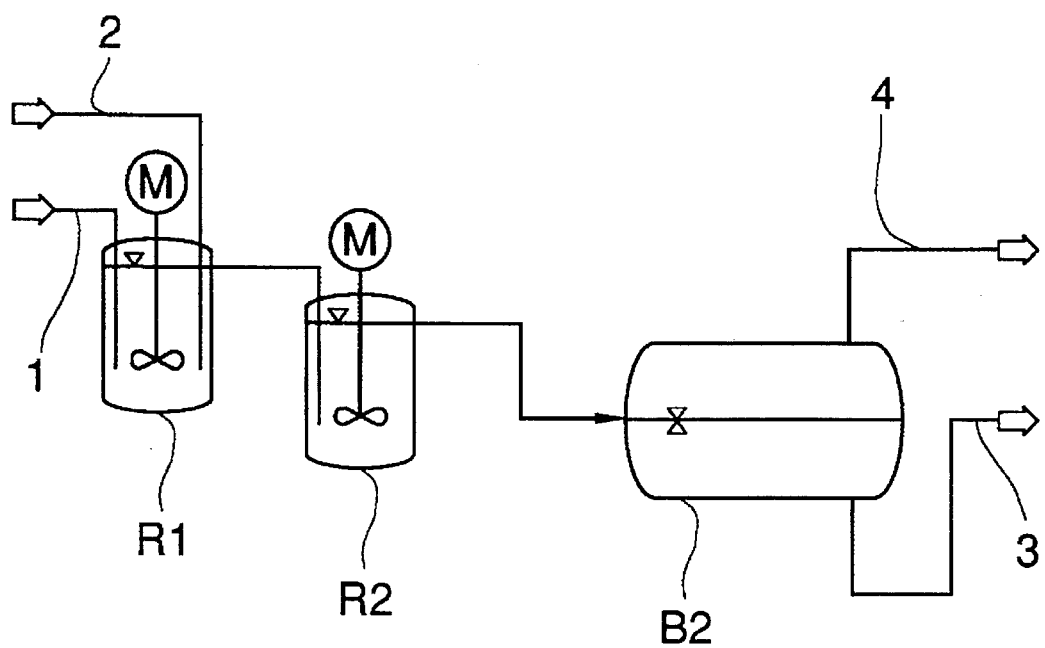

ISOLATION OF TRIPHENYLPHOSPHINE

The present invention relates to a process for isolating triphenylphosphine (TPP) from a triphenylphosphine/aluminum chloride complex dissolved in chlorobenzene by decomplexation, hydrolysis and extraction using water and subsequent separation of the liquid/liquid dispersion, which is composed of a TPP-containing chlorobenzene phase and of an aqueous phase containing Al and Cl compounds, into a TPP-containing chlorobenzene phase and into a TPP-free, aqueous phase, containing Al and Cl compounds.

Triphenylphosphine (TPP) is obtained from triphenylphosphine oxide (TPPO) by halogenation, reduction in chlorobenzene using aluminum to give TPP·⅔ AlCl₃ and subsequent decomplexation and hydrolysis in accordance with the following equation, with the dissolved Al and Cl compounds being extracted together with the water from the TPP-containing chlorobenzene phase:

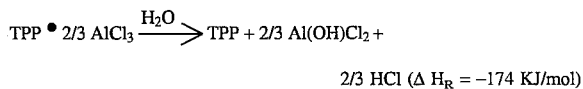

$$2/3 \text{ HCl } (\Delta H_R = -174 \text{ KJ/mol})$$

The extraction is followed by separation of the resulting liquid/liquid dispersion, which is composed of a TPP-containing chlorobenzene phase and of an containing Al and Cl compounds aqueous phase, into a TPP-containing chlorobenzene phase and into a TPP-free, aqueous phase, containing Al and Cl compounds.

This is currently carried out using known extraction apparatuses such as mixer settlers and extraction columns. Irrespective of the mode of operation of these apparatuses, complete separation into the two phases is impossible. Both the chlorobenzene phase and the aqueous phase contain residues of the other phase in the form of fine dispersions.

It is the object of the present invention to develop a process for separating the resulting liquid/liquid dispersion into a TPP-containing chlorobenzene phase and an aqueous phase, each of which is free of foreign phases.

We have found that this object is achieved by a process with the following features:

water is dispersed in the chlorobenzene phase in a ratio of 0.6–0.95 kg of water per kg of chlorobenzene solution in a 1st mixing apparatus in such a way that the temperature resulting from the hydrolysis is in the range from 60° to 90° C., the dispersion being carried out with holdup times of 5–30 minutes and energy densities of 2–10 kW/m³, a post-dispersion is carried out in a 2nd mixing apparatus with residence times of 5–60 minutes and energy densities of 0.05–0.5 kW/m³, and the heavier TPP-containing chlorobenzene phase is separated from the lighter TPP-free, aqueous phase containing Al and Cl compounds in a phase separator.

It is surprising and not predictable that the treatment according to the invention of the liquid/liquid dispersion allows the dispersion to be completely separated in a phase separator into a chlorobenzene phase free of fine dispersions and which contains about 10% by weight TPP and ≦ppm Al and ≦20 ppm Cl, in dissolved form, and into an aqueous phase which is free of fine dispersions and, due to its poor solubility, substantially no TPP.

The crucial criteria for optimizing the process according to the invention are the ratio of the aqueous phase to the organic phase, the temperature control, the average residence time and the energy density.

The process according to the invention is based on dispersion of the aqueous phase, advantageously with a large proportion of disperse phase. This is known to depend on the phase ratio and is achieved in the present case by the ratio of 0.6–0.95 kg of water/kg of chlorobenzene phase.

The temperature of the dispersion has a crucial effect on the phase separation and is adjusted in the range 60°–90° C. by controlling the temperature of the TPP·⅔ AlCl₃-containing chlorobenzene solution and of the water which are fed into it.

One advantage of the process according to the invention is that the dispersion conditions in the 1st mixing apparatus can be suited to mass and heat transfer without compromising the subsequent phase separation.

The times for complete phase separation of the liquid/liquid dispersion are in the range from 5 to 15 minutes.

With high energy densities of 2–10 kW/m³, in particular 5–8 kW/m³, mass and heat transfer take place and simultaneously the generation of a monodisperse dispersion is favored. The post-dispersion under mild conditions in the 2nd mixing apparatus with energy densities of 0.05–0.5 kW/m³, in particular 0.1–0.3 kW/m³, results in coalescence of the fine drops, due to relative motion differences. A dispersion (drop diameter>100 μm) with a narrow spectrum of drop sizes is obtained, which can be completely separated in a phase separator.

The process can be carried out continuously or batchwise. In each case the phase ratios, temperatures, average residence times and energy densities must be as stated.

BRIEF DESCRIPTION OF THE DRAWING

The drawing is a schematic representation of apparatus that is suitable for carrying out the process.

Suitable mixing apparatuses in both stages of the process are stirred vessels equipped with infinitely variable transmissions so that the energy densities can be adapted within the stated limits. Suitable internals are 3-paddle stirrers with a baffle or baffles, which bring about homogeneous mixing and, at the same time, have a low shear action.

The invention is explained hereinafter by means of examples.

EXAMPLE 1

5 kg/h TPP·⅔ AlCl₃-containing chlorobenzene solution (stream 1) from the dehalogenation and 4 kg/h water (stream 2) are continuously fed into the first stirred vessel R1, with an aqueous/ organic phase ratio of 0.8 kg/kg. The chlorobenzene solution is fed at 130° C. and the water at 20° C. The stirrer speed is adjusted so that the energy density is 6 kW/m³. There is submerged entry of both streams near the stirrer, and the resulting dispersion is drawn off by overflow into stirred vessel R2. The average residence time of the dispersion is 8 minutes. The temperature of the dispersion is 130° C. In the stirred vessel R2, which has the same design, the dispersion is stirred at a reduced speed, corresponding to an energy density of 0.15 kW/m³, the average residence time being 8 minutes. The internals in both stirred vessels are 3-paddle stirrers and baffles, which bring about homogeneous mixing and, at the same time, have a low shear action. The coarse dispersion flowing out of stirred vessel R2 (diameter drop about 1000 μm) is fed into the phase separator B2 where spontaneous phase separation occurs. Two clear phases containing no fine dispersion are obtained. The average residence time in the phase separator is 13 minutes. The TPP-containing chlorobenzene phase (stream 3) contains ≦3 ppm Al and ≦20 ppm Cl in dissolved form. The aqueous phase (stream 4) contains no TPP.

EXAMPLE 2

0.4 kg of water is introduced into a 1 l stirred vessel which is equipped with stirrer and baffles as in Example 1. The stirred speed is adjusted so that the energy density is 7.2 kW/m$^3$ 0.5 kg of TPP·⅔ AlCl$_3$-containing chlorobenzene solution is metered in. After all the chlorobenzene solution has been metered in, the dispersion is stirred at the same speed for 5 minutes. The dispersion is subsequently stirred at a reduced speed corresponding to an energy density of 0.15 kW/m$^3$ for 5 minutes. The temperature of the dispersion is about 70° C. After the stirrer is switched off, spontaneous separation of the dispersion takes place. After 5 minutes, both phases are completely clear and contain no fine dispersion. The lower phase is the TPP-containing chlorobenzene phase with $\leq$3 ppm Al and $\leq$20 ppm Cl and the upper phase is the aqueous phase containing no TPP.

We claim:

1. In a process for isolating triphenylphosphine (TPP) from a triphenylphosphine/aluminum chloride complex dissolved in chlorobenzene by decomplexation, hydrolysis and extraction using water and subsequent separation of the liquid/liquid dispersion, which is composed of a TPP-containing chlorobenzene phase and of an aqueous phase containing Al and Cl compounds into a TPP-containing chlorobenzene phase and into a TPP-free, aqueous phase, containing Al and Cl compounds, the improvement which comprises:

dispersing water in the chlorobenzene phase in a ratio of 0.6–0.95 kg of water per kg of chlorobenzene solution in a first mixing apparatus in such a way that the temperature resulting from the hydrolysis is in the range from 60° to 90° C., the dispersion being carried out with residence times of 5–30 minutes and energy densities of 2–10 kW/m$^3$, carrying out a second dispersion step in a second mixing apparatus with residence times of 5–60 minutes and energy densities of 0.05–0.5 kW/m$^3$ to form dispersed drops having a diameter greater than >100 μm, and separating the heavier TPP-containing chlorobenzene phase from the lighter TPP-free, aqueous phase containing Al and Cl compounds in a phase separator.

2. The process of claim 1, wherein energy densities of 5–8 kW/m$^3$ are used in the first mixing apparatus and energy densities of from 0.1–0.3 kW/m$^3$ is used in the second mixing apparatus.

* * * * *